(12) United States Patent
Chaudhari et al.

(10) Patent No.: US 8,252,963 B2
(45) Date of Patent: Aug. 28, 2012

(54) NANO-METAL CATALYSTS FOR POLYOL HYDROGENOLYSIS

(75) Inventors: Raghunath V. Chaudhari, Lawrence, KS (US); Debdut S. Roy, Lawrence, KS (US); Bala Subramaniam, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 261 days.

(21) Appl. No.: 12/797,084

(22) Filed: Jun. 9, 2010

(65) Prior Publication Data

US 2010/0317901 A1     Dec. 16, 2010

Related U.S. Application Data

(60) Provisional application No. 61/185,490, filed on Jun. 9, 2009.

(51) Int. Cl.
*C07C 29/00* (2006.01)
*B01J 23/46* (2006.01)
*B01J 31/02* (2006.01)
*B01J 27/188* (2006.01)

(52) U.S. Cl. ........ 568/861; 568/903; 502/158; 502/185; 502/210; 502/261; 502/325

(58) Field of Classification Search .................. 568/861, 568/903; 502/158, 185, 210, 261, 325, 332
See application file for complete search history.

(56) References Cited

U.S. PATENT DOCUMENTS

| | | | |
|---|---|---|---|
| 3,963,788 A | 6/1976 | Kruse et al. | |
| 4,273,680 A | 6/1981 | Halluin | |
| 4,503,274 A | 3/1985 | Arena | |
| 5,354,914 A | 10/1994 | Gubitosa et al. | |
| 5,403,805 A | 4/1995 | Gubitosa et al. | |
| 2007/0135301 A1 | 6/2007 | Holcomb, Jr. | |

OTHER PUBLICATIONS

International Search Report dated Feb. 1, 2011 as issued in connection with corresponding PCT Application No. PCT/US2010/037948, filed on Jun. 9, 2010.

*Primary Examiner* — Sikarl Witherspoon
(74) *Attorney, Agent, or Firm* — Stinson Morrison Hecker LLP

(57) ABSTRACT

A catalyst composition can include: a support; a ruthenium catalyst (Ru) nanoparticle; and a linker linking the Ru nanoparticle to the support, wherein the linker is stable under hydrogenolysis conditions. In one aspect, the linker can include 3-aminopropyl trimethoxysilane (APTS) or derivatives thereof, such as those with amine functionality. In another aspect, the linker can include phosphotungstic acid (PTA) or other similar solid acid agents. In another aspect, the support can be selected from alumina, carbon, silica, a zeolite, $TiO_2$, $ZrO_2$, or another suitable material. A specific example of a support includes zeolite, such as a NaY zeolite. The Ru nanoparticle can have a size range from about 1 nm to about 25 nm, and can be obtained by reduction of Ru salts.

30 Claims, 7 Drawing Sheets

Cellobiose: 2g
Catalyst: 0.25g
Temp: 393K
$P_{H2}$: 41 bar
Liq. Volm: 30 ml
Time: 6h

NANO-METAL CATALYSTS FOR POLYOL HYDROGENOLYSIS

CROSS-REFERENCE

This patent application claims benefit of U.S. provisional patent application 61/185,490, filed Jun. 9, 2009, which provisional application is incorporated herein by specific reference in its entirety.

BACKGROUND

The chemistry of catalyst preparation has become important in industry due to the large number of processes that catalyzed reactions. Investigations into catalyst preparation have explored different catalyst materials, catalyst combinations, and the chemistry of linking a catalyst to a support. Often, however, a catalyst may be functional in a process, but the catalyst is not active enough or stable under the requisite reaction conditions. For example, polymers have been used to link catalyst materials to supports, which may be useful for some catalytic reactions. On the other hand, the same catalyst material may be useful in a catalytic reaction that has higher temperature and/or pressure operating conditions where the polymer linker is not stable. Thus, there still remains a need to improve the chemistry of catalyst preparation to achieve stable catalysts that can operate at a wide range of temperatures and pressures as well as at the higher end of operating temperatures and pressures. Many reactions require high temperatures and pressures to achieve catalyst productivity desirable for practical applications, and hence one of the goals in catalysis research is to develop catalytic materials that will work at lower temperatures and pressures without affecting the performance. For example, reducing the metal particle size to nano-scale can enhance the active metal surface area for the same bulk composition of the metal in a catalyst and lead to increased activity and in some cases a selectivity of the products.

SUMMARY

In one embodiment, a catalyst composition can include: a support; a ruthenium catalyst (Ru) nanoparticle; and a linker linking the Ru nanoparticle to the support, wherein the linker is stable under hydrogenolysis conditions. In one aspect, the linker can include 3-aminopropyl trimethoxysilane (APTS) or derivatives thereof, such as those with amine functionality. In another aspect, the linker can include phosphotungstic acid (PTA) or other similar solid acid agents. In another aspect, the support can be selected from alumina, carbon, silica, a zeolite, $TiO_2$, $ZrO_2$, or another suitable material. A specific example of a support includes zeolite, such as a NaY zeolite. The Ru nanoparticle can have a size range from about 1 nm to about 25 nm, and can be obtained by reduction of Ru salts.

In one embodiment, the catalyst composition can include a plurality of Ru catalysts linked to the support through a plurality of linkers. In one aspect, the Ru catalysts are linked to the support in a distribution configured to inhibit agglomeration of the Ru catalysts.

In one embodiment, the support is a macro support structure. A macro support structure has a size that is too large to prepare a slurry because the macro support structure is too large to be entrained into a fluid without significant agitation, and once set the macro support structure quickly settles. The macro support structure has a dimension greater than about 1 micron or greater. The support can be particles on the order of about 10 microns to about 1000 microns, from about 50 microns to about 500 microns, from about 75 microns to about 250 microns, or about 100 microns, which can be used for slurry reactions. Alternatively, the support can be much larger and in the form of pellets having a dimension about 0.20 to about 5 cm, about 0.30 to about 2 cm, or about 0.35 cm to about 1 cm, or about 0.5 to about 1 cm (e.g., ⅛-3/16 inch). These sizes can be suitable for packed-bed reactors. The macro support structure can be porous with pore sizes on the order of a few nanometers (e.g., 2, 5, or 10 nm, or range therebetween) to few tens of Angstroms (e.g., 10, 20, or 50 or range therebetween.

In one embodiment, the linker is stable at temperatures ranging from about 80° C. to about 600° C., about 100° C. to about 400° C., about 150° C. to about 300° C., about 200° C. to about 250° C.

In one embodiment, the catalyst composition can be combined with a reaction composition. The reaction composition can include a reactant that can undergo a hydrogenolysis reaction to reduce the number of hydroxyl groups. The reactant can include a cellulose, cellobiose, polyol, or dehydration product thereof. In one aspect, the reaction composition can include water as a solvent, and various water/solvent combinations can be used. In one aspect, the water/solvent composition can include an alcohol as the co-solvent. Examples of alcohol co-solvents such as C1-C3 alcohols, methanol, ethanol, isopropanol, and combinations thereof.

In one embodiment, an acid is included in the reaction condition to facilitate the hydrogenolysis reaction. The acid can be inorganic or organic. Examples of the acids can include hydrochloric acid, sulfuric acid, nitric acid, acetic acid, oxalic acid, p-toluene sulfonic acid, and combinations thereof.

In one embodiment, a hydrogenolysis process can include: providing a catalyst composition as described herein; combining the catalyst with liquid phase reactants having one or more of water, an alcohol, or an acid and with a reactant selected from cellulose, cellobiose, polyol, dehydration product thereof, or combinations thereof; introducing hydrogen into the reaction liquid; and reacting the reactant with the catalyst in the presence of hydrogen to form an alcohol, lower polyol, or higher polyol, wherein cellulose and cellobiose reactants form higher polyols, and polyol and polyol dehydration products form alcohols and lower polyols.

In one embodiment, the reactant in the reaction liquid can range from about 0.5% to about 20%, about 1% to about 15%, or about 5% to about 10% by weight or volume of the reaction liquid.

In one embodiment, the alcohol in the reaction liquid can range from about 20% to about 60%, about 30% to about 50%, or about 35% to about 45% by weight or volume of the reaction liquid.

In one embodiment, the acid in the reaction liquid can range from about 0.5% to about 10%, about 1% to about 5%, or about 2% to about 4% by weight or volume of the reaction liquid.

During the hydrogenolysis process, the reaction can be conducted at a temperature from about 80° C. to about 600° C., about 100° C. to about 400° C., about 150° C. to about 300° C., about 200° C. to about 250° C.

Also, during the hydrogenolysis process, the reactions can be conducted at a pressure of about 1 bar to about 400 bar, about 10 bar to about 300 bar, or about 20 bar to about 200 bar.

The hydrogenolysis process can provide conversion of the limiting reactant is greater than about 80 mole %, 90 mole %, 95 mole %, 100 mole % or ranges there between.

The hydrogenolysis process can provide selectivity in conversion of the cellulose or cellobiose to sorbitol ranges from about 40 mole % to about 80 mole %, about 50 mole % to 75 mole %, or about 60 mole % to about 65 mole %.

In one embodiment, the present invention can include a method of manufacturing a catalyst composition as described herein. Such a method can include: providing a support; providing a Ru nanoparticle; and linking a linker to the Ru nanoparticle and to the support so as to link the Ru nanoparticle to the support, wherein the linker is stable under hydrogenolysis conditions. The linker can be 3-aminopropyl trimethoxysilane and/or phosphotungstic acid.

In one embodiment, the Ru nanoparticle is prepared. An example of a method for preparing the Ru nanoparticle is by reducing a Ru salt.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1B is a close-up of FIG. 1A at about 2× magnification over FIG. 1A.

DETAILED DESCRIPTION

Figure 1A:
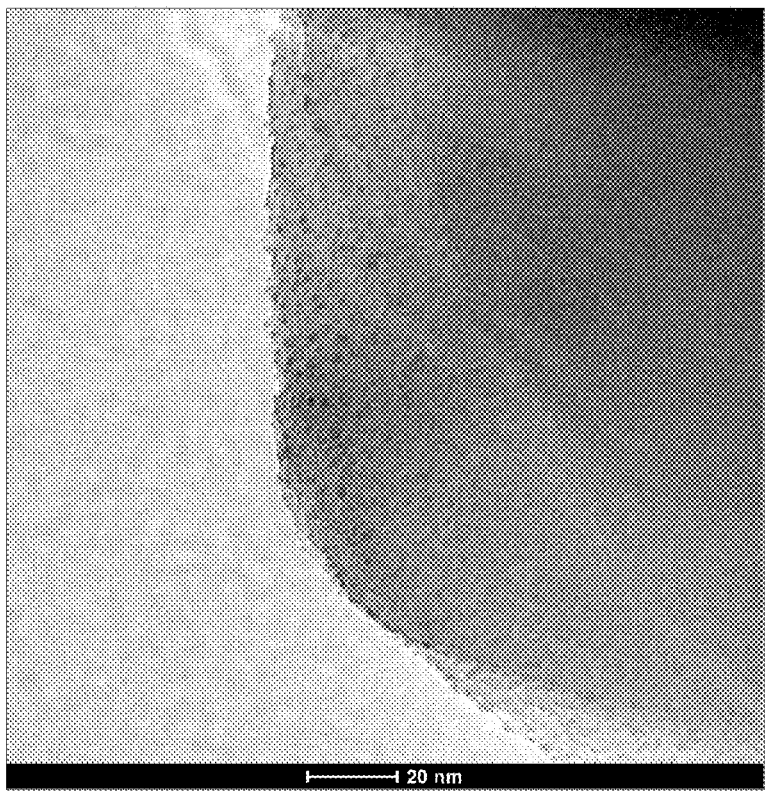
FIG. 1A-1B are TEM images of the anchored Ru nano-catalyst, where

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Figure 2A:
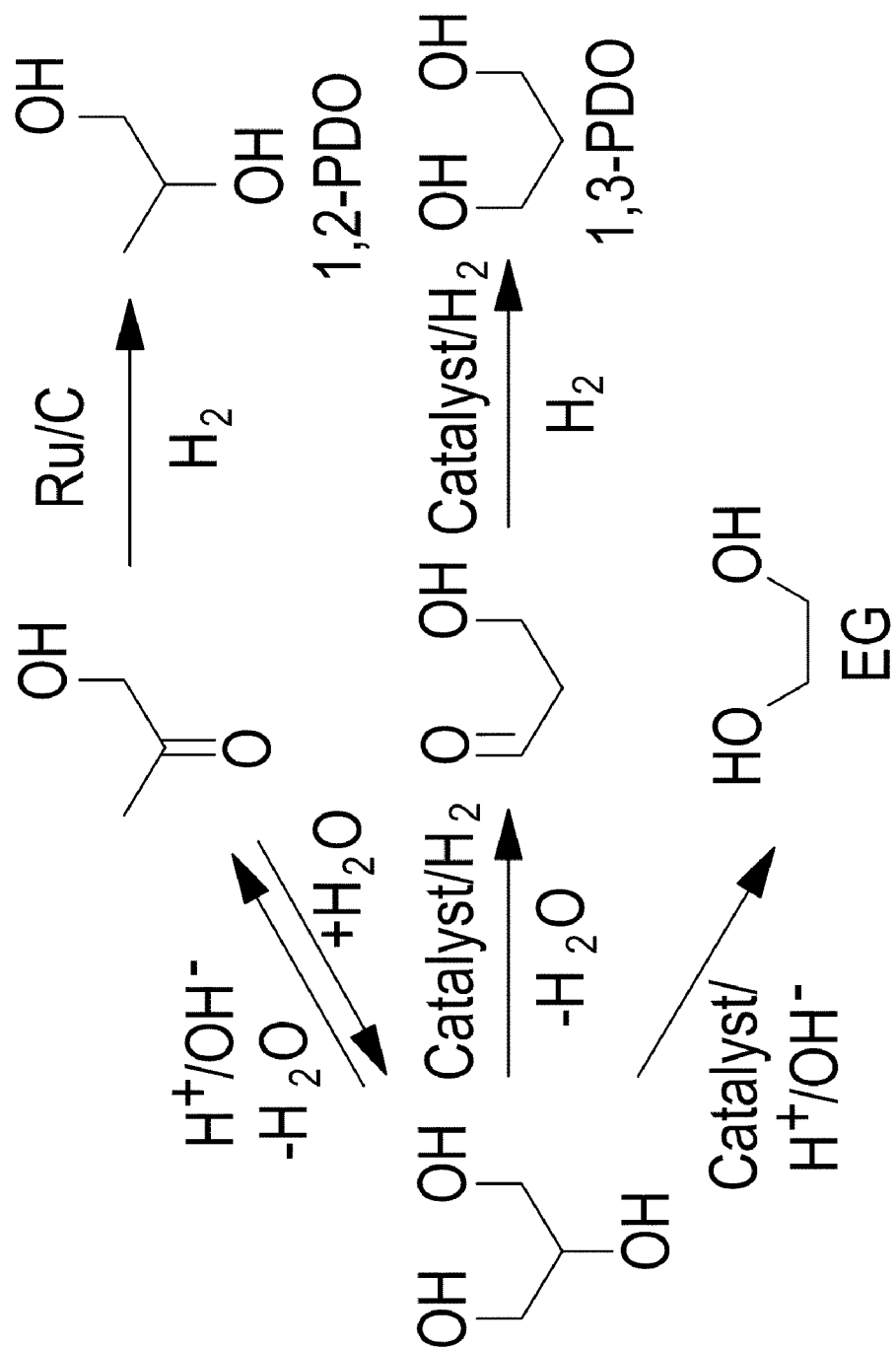
FIG. 2A is a schematic of an example of a chemical reaction that can be catalyzed with the anchored Ru nano-catalyst.
Figure 2B:
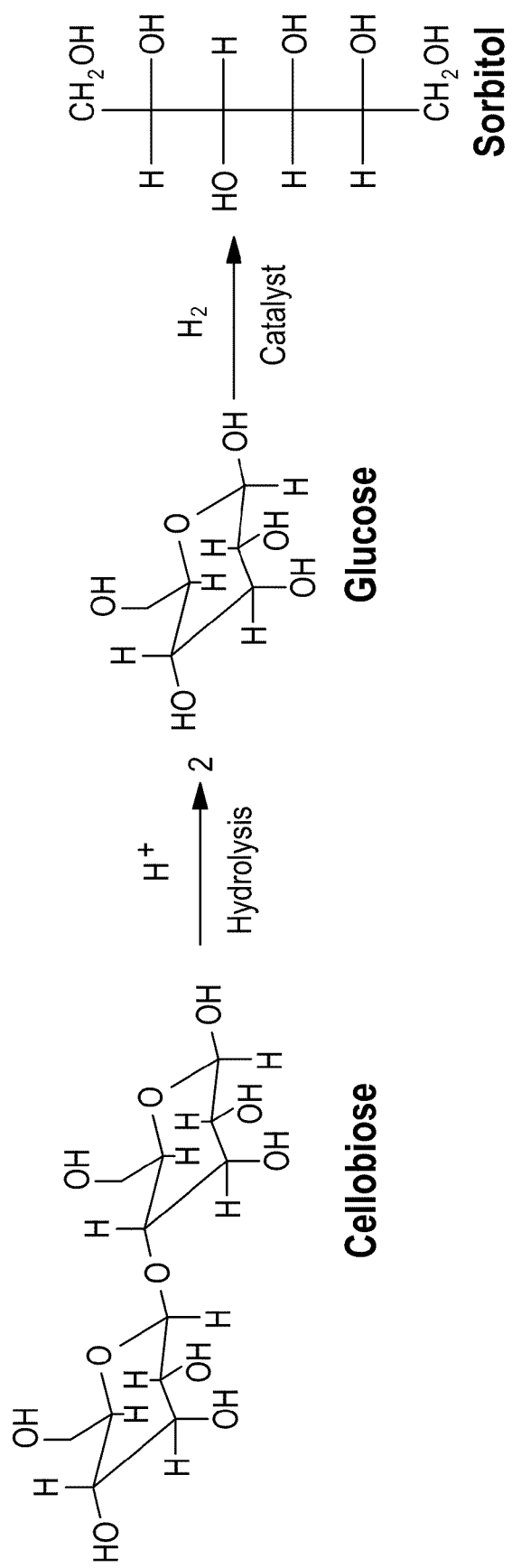
FIG. 2B is a schematic of an example of a chemical reaction for conversion of cellobiose to sorbitol.

Generally, the present invention includes a novel catalyst composition that includes a nano scale ruthenium catalyst (e.g., nanoparticle) linked to a support through a thermally stable linker. The linker can withstand the conditions of hydrogenolysis without significant degradation. The invention also includes methods of synthesis of the catalyst as well as methods of performing hydrogenolysis with the catalyst. Synthesis of a novel catalyst can include linking a nano scale Ru catalyst to a support through a phosphotungstic acid linker and/or 3-aminopropyl trimethoxysilane linker. Methods of hydrogenolysis can include reacting a polyol reactant with hydrogen in the presence of the catalyst. Examples of the polyol reactant can include cellulose, cellobiose, sorbitol, glucose, glycerol, or other polyol. The typical reaction scheme for hydrogenolysis of glycerol is shown in FIG. 2A; while the reaction scheme for hydrogenolysis of cellobiose to sorbitol is shown in FIG. 2B.

In one option, the catalyst includes nanoparticles of Ru metal immobilized on a support (e.g., NaY zeolite) using 3-aminopropyl trimethoxysilane as a linking agent that reacts with the support to form a linker (i.e., the functionalized support to facilitate linking of active nano-metal to the support) that anchors the Ru metal to the zeolite. In another option, the catalyst includes nanoparticles of ruthenium metal immobilized on a support (e.g., NaY zeolite) using phosphotungstic acid as a linking agent that reacts with the support and the Ru particle to form a catalyst in which Ru metal anchors to a functionalized zeolite support.

The linking agent can include 3-aminopropyl trimetholxysilane or any derivative thereon that includes amine functionality. Some examples include 2-aminoethyl trimethoxysilane, 4-Aminobutyl trimethoxysilane, [3-(2-aminoethylamino)propyl]-trimethoxysilane, 3-[2-(2-Aminoethylamino)-ethylamino]propyl-trimethoxysilane, combinations thereof, or the like.

The linking agent can include phosphotungstic acid or other similar solid acid agents. Some examples include molybdophosphoric acid, tungstosilicic acid, molybdosilicic acid, combinations thereof, and the like.

The nano scale particle size of the Ru metal can range from about 0.1 nm to about 1 micron, from about 1 nm to about 500 nm, about 1.5 nm to about 100 nm, 1.75 nm to about 50 nm, about 2 nm to about 25 nm, about 3 nm to about 20 nm, and about 4 nm to about 10 nm, or any ranges between any of the aforementioned values.

In one embodiment, the support can be alumina, carbon, silica, a zeolite, or another suitable material. An example can include a NaY zeolite. The size of the support can be any feasible size larger than 1 micron, which theoretically can range to about 20 to 50 meters depending on the industrial scale. In the lower size range, the support can have a dimension that is from about 1 micron to about 10 cm, 10 micron to about 1 cm, 100 microns to about 10 mm, or about 1 mm to 5 mm, or any ranges between any of the aforementioned values.

The Ru catalyst can be used in a process for efficiently converting cellulosic materials to polyols in a single pot through hydrogenolyis, as well as converting higher polyols to lower polyols through hydrogenolysis. The hydrogenolysis can include a system having a Ru nanoparticle catalyst anchored to a support with the reactant in a solvent. The solvent can be water or a modified aqueous solvent system.

For example, hydrogenolysis of cellulosic materials can be carried out in an aqueous medium, and the reactions may be limited by hydrogen availability in the liquid phase. As such, a modified aqueous solvent can include a co-solvent that improves hydrogen content in the liquid. Alcohols can be used as the co-solvents along with water to improve the hydrogen solubility in the liquid phase, and can improve the hydrogenolysis efficiency in the presence of a Ru catalyst.

Previous processes used water as a solvent which has poor hydrogen solubility. Therefore, very often the activity and selectivity to sorbitol were not very high or it required very high hydrogen pressure conditions. The solvent system having water and methanol improves hydrogen solubility, and when combined with the novel Ru catalyst, gives an efficient catalyst-solvent system for hydrogenation of glucose to sorbitol. Low solubility of hydrogen and hence low selectivity to sorbitol (~12%) was confirmed by a run without methanol as a co-solvent with water, otherwise identical reaction conditions. Glucose was identified as the major product in this run with ~80% selectivity.

In one embodiment, the solvent system can include water and an alcohol as well as a promoter of hydrolysis of the reactant. The promoter can include an acid, such as an inorganic or organic acid. The inorganic acid can include hydrochloric acid, sulfuric acid, or nitric acid. The organic acid can include acetic acid, oxalic acid, or p-toluene sulfonic acid. Other inorganic or organic acids may be used.

For example, a mineral acid (e.g., HCl) can be added to the solvent system as a promoter to hydrolyze the cellulosic material to its monomers. The monomers that are produced in the solvent system can be further reacted through hydrogenolysis to form polyols. The increased solubility of hydrogen in the liquid phase of the solvent system can provide increased conversion of the monomers to polyols. Preliminary results with alcohol as a co-solvent with water showed substantial improvement in polyol selectivity in the presence of the novel Ru catalyst compared to the experiments without a co-solvent.

The hydrogenolysis process using the novel Ru catalyst can provide high conversion for cellobiose (e.g., about 100%) to sorbitol (e.g., about 78.8%) in a single processed composition. The conversion of cellobiose to sorbitol involves two steps, which can now be combined and performed in the same reaction mixture. In the first step, cellobiose is hydrolyzed in the presence of an acidic promoter to glucose, and in the second step the produced glucose is hydrogenated to sorbitol in the presence of a suitable catalyst. The second step can be facilitated with a good hydrogenation catalyst (e.g., novel Ru catalyst), and high solubility of hydrogen in the liquid phase (e.g., obtained by water/alcohol solvent system).

While the process can be described with cellobiose as a reagent, the process may also be useful for converting any cellulosic materials to polyols. The polyols can be used for hydrogen production by aqueous phase reforming for fuel cell applications. Also, the polyols can undergo hydrogenolysis into lower polyols and alcohols.

Now, selectivity to sorbitol from cellobiose can be improved with the novel Ru catalyst (e.g., Ru nano-particles immobilized on a solid matrix using phosphotungstic acid or 3-aminopropyl trimethoxysilane as anchoring agents) and a solvent system having water, an alcohol and an acid. The acid acts to hydrolyze the cellulosic material to its monomers (e.g., glucose), which then undergoes hydrogenolysis with externally added hydrogen to produce sorbitol at about 80% conversion. Accordingly, including alcohol as a co-solvent can increase sorbitol selectivity from 12% (e.g., without alcohol) to about 80% with alcohol.

Also, the novel Ru catalyst can be used for hydrogenolysis of various polyols (e.g., higher polyols) to alcohols or lower alcohols with external hydrogen being added. As used herein the polyol reactant has more hydroxyl groups than the hydrogenolysis product. As such, the reactant polyol can be a "higher polyol" that has a higher number of hydroxyl groups compared to the reaction product that is an alcohol (e.g., single hydroxyl) or "lower polyol" that has a lower number of hydroxyl groups compared to the reactant polyol. For example, the hydrogenolysis of a polyol reactant can result in a hydrogenolysis product that is a lower polyol having one less hydroxyl group or two or more fewer hydroxyl groups. In a specific example, the novel Ru catalyst can facilitate hydrogenolysis of biomass cellulosic material to sorbitol. In another example, hydrogenolysis of glycerol can produce 1,2-propanediol (1,2-PDO), which shows a hydrogenolysis that reduces a triol to a diol.

In one embodiment, the novel Ru catalyst can be used in a reaction protocol with the reactant being biomass, derivatized biomass, or partially-processed biomass to result in polyols and carboxylic acids. The obtained polyols and carboxylic acids, can then be further reacted through catalyzed hydrogenolysis with hydrogen. Suitable biomass products or starting reagents for conversion to chemicals and fuels can include succinic acid, 2,5-furandicarboxylic acid, 3-hydroxypropionic acid, aspartic acid, glucaric acid, glutamic acid, itaconic acid, levulinic acid, 3-hydroxybutyrolactone, glycerol, sorbitol, xylitol, or the like.

In one embodiment, a reaction mixture can be a liquid phase composition that includes a polyol, water, acid, and the novel Ru catalyst. In one aspect, the polyol can be selected from glycerol, glucose, sorbitol, mannitol, fructose, cellobiose, or any polyhydroxy compound. In another aspect, the polyol content can range from 1 to 100% by weight or volume of the liquid phase composition.

During the reaction, the reactant (e.g., cellulosic material or polyol) can be present from about 0.25% to about 30% by weight or volume of the reaction mixture, of about 1% to about 15%, or about 5% to about 10% by weight or volume.

When the reaction begins with a cellulosic material, the acid can range from about 0.25% to about 10% by weight or volume, or about 1% to about 5% by weight or volume, or about 2% to 3% by weight or volume of the total liquid volume of the reaction mixture.

During the reaction, the reaction mixture can be held at a temperature of about 80° C. to about 400° C., about 100° C. to about 350° C., about 150° C. to about 300° C., about 200° C. to about 250° C. for hydrogenolysis. For example, a temperature of about 80° C. to about 130° C. or the other ranges recited herein can be used for the reaction step of hydrolyzing of the cellulosic materials to their monomers as well as hydrogenolysis. The same temperature may be maintained through the hydrogenolysis of the cellulosic monomer to a polyol.

Also, during the hydrogenolysis process, the reaction can be conducted at a pressure of about 1 bar to about 300 bar, about 10 bar to about 200 bar, or about 20 bar to 100 bar. A specific example can include the reaction being conducted under about 14 to about 70 bar partial pressure of hydrogen.

The hydrogenolysis process can provide conversion of the limiting reactant is greater than about 80 mole %, 90 mole %, 95 mole %, 100 mole % or ranges therebetween.

The hydrogenolysis process can provide selectivity in conversion of the cellulose or cellobiose to sorbitol ranges from about 40 mole % to about 80 mole %, about 50 mole % to 75 mole %, or about 60 mole % to about 65 mole %.

In one embodiment, the catalyst can be used for a plurality of different reactions with different reactants. The structure of the catalyst being physically coupled to the support prevents agglomeration of the Ru catalysts surfaces, and thereby inhibits deactivation. This allows the catalyst to be used repeatedly without significant loss of catalytic activity.

EXAMPLES

The nano-metal Ru catalysts can be immobilized on different supports using anchoring techniques with 3-aminopropyl trimethoxysilane or derivatives thereof (e.g., having amine functionality) or with phosphotungstic acid (PTA) or other similar solid acid agents. The hydrogenolysis can be carried out in a 100 ml Parr autoclave and the liquid phase samples can be analyzed using HPLC. The gas phase samples can be analyzed at the end of the reaction using GC.

Synthesis of 3-aminoproply trimethoxysilane (APTS) anchored Ru nanoparticles on NaY zeolite: 5.73 mmol of APTS was added drop wise in a slurry of NaY zeolite in anhydrous dichloromethane at room temperature and the slurry was stirred for 16 hrs. The solid (APTS-Y) was then filtered, washed several times with anhydrous dichloromethane and dried under vacuum. To immobilize the Ru nanoparticles using APTS-Y, colloidal Ru nanoparticles were first synthesized by reducing a 100 ml $10^{-4}$ M ruthenium chloride salt solution using 0.01 g of sodium borohydride at room temperature. 0.02 g of APTS-Y was added into the Ru colloidal solution and stirred for 12 hrs at room temperature. The gray solid (Ru-APTS-Y) was allowed to settle, filtered, washed with hot water and dried under vacuum.

Synthesis of phosphotungstic acid (PTA) anchored Ru nanoparticles on NaY zeolite: 0.2880 gm phosphotungstic acid dissolved in 15 ml anhydrous ethanol was added in a slurry of NaY zeolite in 45 ml anhydrous ethanol and stirred for 12 hrs in an inert atmosphere at room temperature. The white solid (PTA-Y) was filtered, washed with ethanol and dried under vacuum. A 100 ml aqueous Ru salt solution of $10^{-4}$ M strength was reduced using sodium borohydride to form colloidal Ru nanoparticles and PTA-Y was added to it to immobilize the metal nano-particles. The suspension was stirred for 16 hrs and then the solid was filtered (Ru-PTA-Y), washed and dried under vacuum.

Figure 1B:
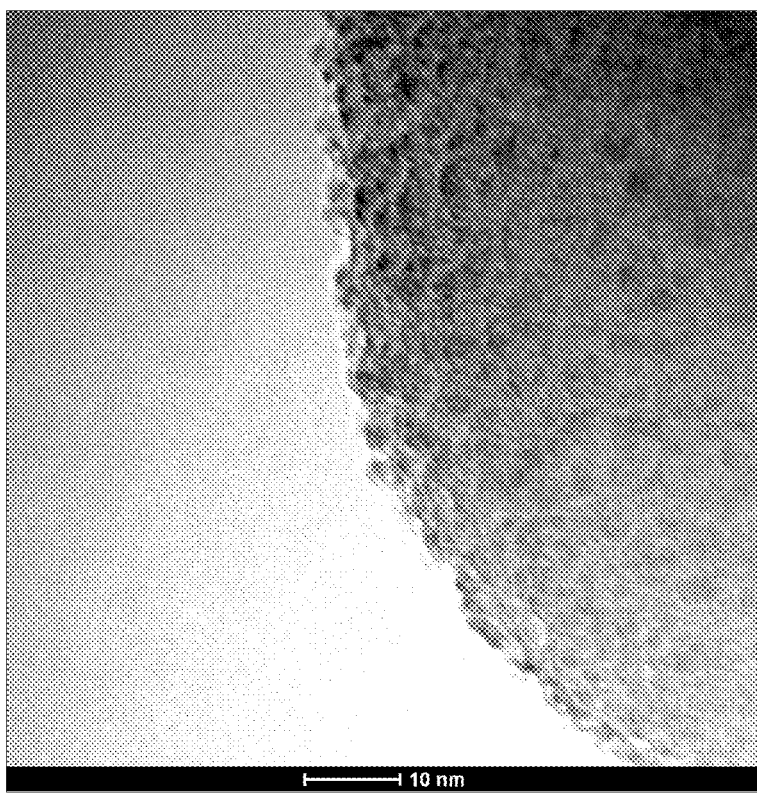

The anchored Ru-PTA-Y nano-metal catalysts were characterized by XRD, TEM, EDAX, and CP-MAS-NMR to elucidate the structure of the synthesized material. A typical TEM image of the anchored Ru nano-catalyst is shown in FIGS. 1A-1B, which shows the uniform dispersion of the Ru nanoparticles on the solid support.

Figure 4:
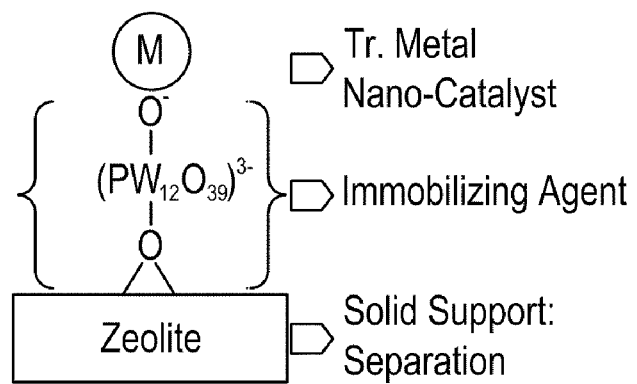
FIG. 4 shows an example of a catalyst (Ru) linked to a support (NaY zeolite) with a stable linker (PTA).

FIG. 4 shows an example of a catalyst (Ru) linked to a support (NaY zeolite) with a stable linker (PTA).

Figure 5:
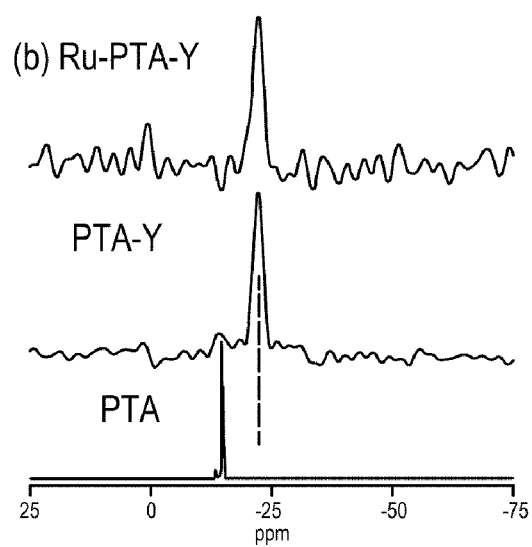
FIG. 5 shows $^{31}P$ CP-MAS NMR of the PTA, PTA-Y, and Ru PTA-Y catalyst.

FIG. 5 shows $^{31}$P CP-MAS NMR of the PTA, PTA-Y, and Ru PTA-Y catalyst.

The immobilized nano-metal Ru catalysts were tested for hydrogenolysis of glycerol and cellobiose (e.g., a dimmer of glucose). For comparison with conventional heterogeneous catalysts, the reactions were carried out at the identical conditions with commercial Pt, Pd, Ru and Rh catalysts. The influence of alkali promoter (e.g., NaOH) was also tested for the impact on hydrogenolysis reactions. Ethylene glycol (EG), 1,2- and 1,3-PDO (propanediol) were found to be the major products in all the cases.

The obtained results are attributed to catalyst design and high metal dispersion characteristics.

Briefly, the above hydrogenolysis experiments were carried out in a high pressure (up to 3000 psi), high temperature (573 K) Parr autoclave. The autoclave was equipped with a heating arrangement, overhead stirrer, thermo well, pressure gauge as well as a pressure transducer, gas inlet, gas outlet, sampling valve and a rupture disc. There was a separate controller for agitation speed and temperature. The temperature, pressure in the reactor as well as in the reservoir for hydrogen were logged in after each 5 seconds through data acquisition software.

Figure 3:
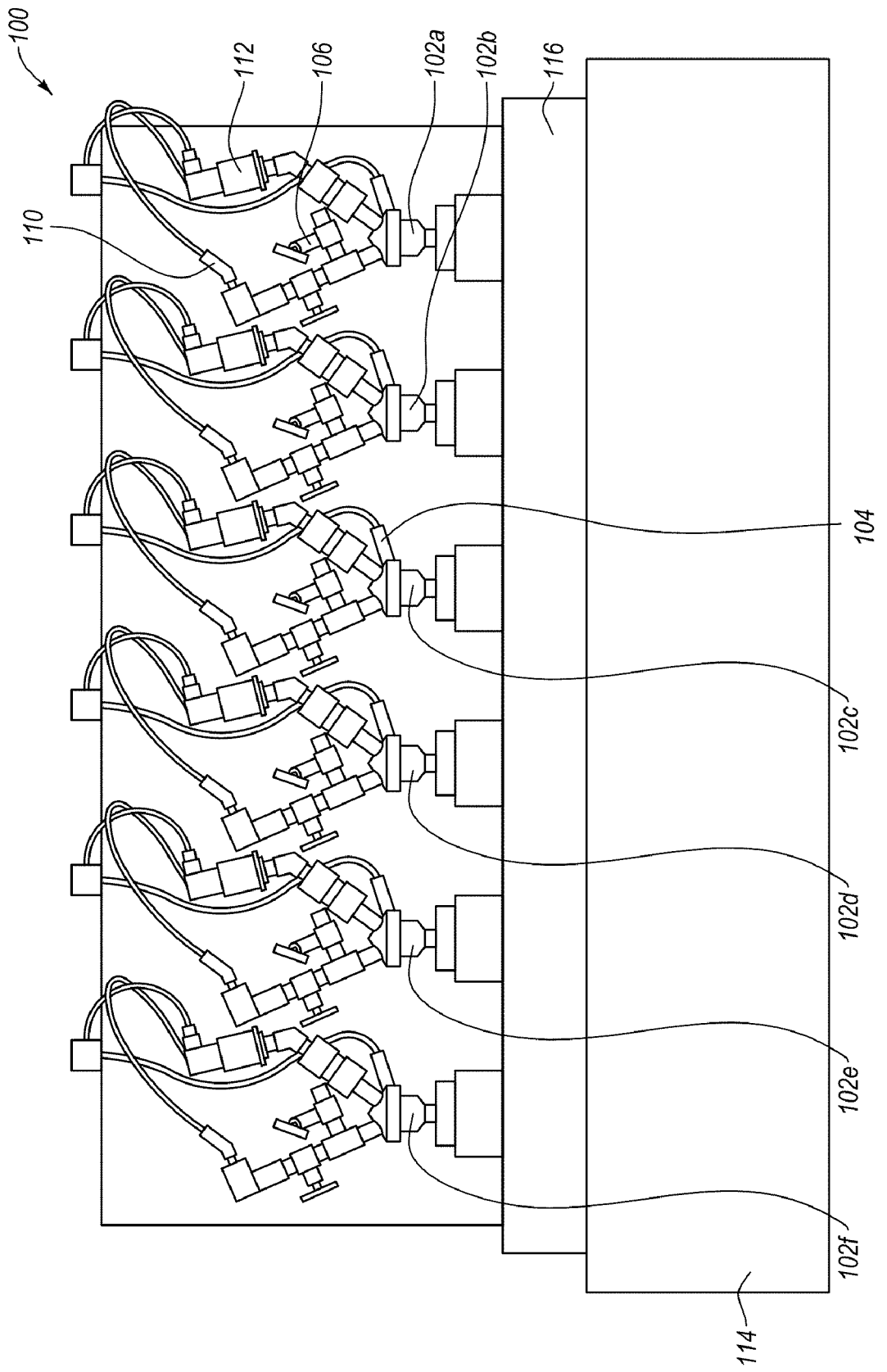
FIG. 3 is a schematic diagram of a reactor system that can include the anchored Ru nano-catalyst.

A schematic of the slurry reactor system 100 for the experiments are shown in FIG. 3. The catalytic hydrogenolysis of glycerol was carried out in a high pressure, high temperature multiple slurry reactor system 100 (FIG. 3) supplied by Parr Instrument Co., Moline, Ala. The reactor system 100 includes a parallel array of six autoclave reactors 102a-f that can be operated simultaneously at different temperatures and pressures. Each autoclave reactor 102 is equipped with a thermowell 104, pressure transducer 106, gas inlet 108, gas outlet 110, and a rupture disc 112. A magnetic stirrer system 114 with maximum agitation speed of 30 Hz provides mixing in each reactor 102. The temperatures and pressures in the individual reactors 102 are independently controlled and monitored with a computer (not shown) interfaced with the control module 116 of the reactor system 100. The common agitation speeds of the reactors 102 can be controlled from the computer interface or with the manual controller (not shown) in the reactor setup itself. The temperature and pressure of the reactors 102 as well as the hydrogen are logged every 5 seconds through SpecView data acquisition software.

The details of the HPLC method are as follows: Rezex ROA-Organic Acid H+ (8%) column (300×7.8 mm), mobile phase: 0.005 N aqueous $H_2SO_4$, flow rate: 0.5 ml/min, oven temperature: 60° C., detector: RID, run time: 30 min. The gas phase was analyzed using two columns; the details of which are as Table 1.

TABLE 1

| Parameters | Column 1 | Column 2 |
|---|---|---|
| Column | 60/80 Carboxen 1000 (packing material: carbon molecular sieve) (4.5 m × 2.1 mm) film thickness 0.50 μm | Haysep DB (packing material: Divinylbenzene) (2.5 m × 3.1 mm) film thickness 0.25 μm |
| Oven | 100° C. (hold for 8 min)— then ramped 30° C./min to 200° C. (hold for 14 min) | |
| Run time | 26 min | |
| Detector | TCD (250° C.) | FID (275° C.) |
| Carrier gas | He (50 sccm) | He (35 sccm) |

Typical concentration-time profiles for fresh and used 5% $Ru/Al_2O_3$ catalysts for glycerol hydrogenolysis at 473 K are shown in FIG. 4. The results show that the $Ru/Al_2O_3$ catalyst is deactivated during the run and the reaction rate slows down significantly as the time proceeds. As such, improvements over $Ru/Al_2O_3$ catalyst were found with the anchored Ru-nanocatalyst.

Additionally, the Ru-PTA-Y catalyst was compared to Ru/Al2O3 catalyst prepared by conventional methods. The results shown in Table 2 below indicate that Ru-PTA-Y is a superior catalyst.

TABLE 2

| | Ru-PTA-Y | | $Ru/Al_2O_3$ | |
|---|---|---|---|---|
| | Conc. kmol/m$^3$ | C Selectivity, % | Conc. kmol/m$^3$ | C Selectivity, % |
| | Liquid phase products | | | |
| Glycerol | 0.521 | 53.44 (Conv. %) | 0.537 | 52.03 (Conv. %) |
| EG | 0.108 | 12.04 | 0.096 | 10.96 |
| 1,2-PDO | 0.227 | 37.95 | 0.139 | 23.87 |
| 1,3-PDO | 0 | 0 | 0 | 0 |
| LA | 0.024 | 4.01 | 0.027 | 4.64 |
| MeOH | 0.008 | 0.04 | 0.004 | 0.02 |
| EtOH | 0.007 | 0.79 | 0.006 | 0.67 |
| IPA | 0.006 | 0.93 | 0.005 | 1.47 |
| 1-Propanol | 0 | 0 | 0 | 0 |

TABLE 2-continued

| | Ru-PTA-Y | | Ru/Al$_2$O$_3$ | |
|---|---|---|---|---|
| | Conc. kmol/m$^3$ | C Selectivity, % | Conc. kmol/m$^3$ | C Selectivity, % |
| Gas phase products | | | | |
| Methane | 0.185 | 24.15 | 0.241 | 32.16 |
| Ethane | 0.003 | 0.80 | 0.039 | 10.54 |
| Propane | 0.001 | 0.19 | 0.006 | 2.508 |
| n-butane | 9.9 × 10$^{-5}$ | 0.05 | 0.002 | 0.99 |
| n-Pentane | 0 | 0 | 5.8 × 10$^{-5}$ | 0.04 |
| CO | 0.006 | 0.81 | 0.006 | 0.84 |
| CO$_2$ | 0.065 | 8.42 | 0.107 | 14.21 |
| MeOH | 0.001 | 0.14 | 0.001 | 0.16 |
| | Error: 2.21% | Total: 95.3% | Error: −1.76 | Total: 103.1% |

Figure 6:
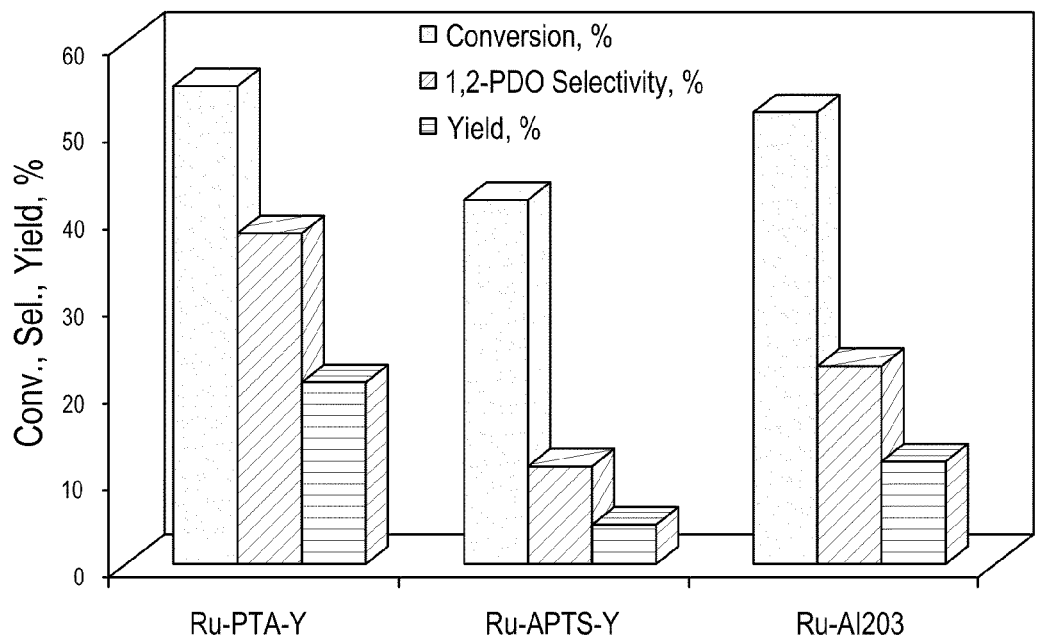
FIG. 6 shows glycerol hydrogenolysis with Ru-PTA-Y, Ru-APTS-Y, and Ru/Al$_2$O$_3$. The reaction conditions were as follows: Glycerol: 3 g (10 wt %); Catalyst: 0.25 g; Temp.: 200° C. (473 K); P$_{H2}$: 41 bar; Solvent: H$_2$O; Liq. Volume: 30 ml; and Time: 6 hours.

The Ru-PTA-Y, Ru-APTS-Y, and Ru/Al$_2$O$_3$ were studied with respect to glycerol hydrogenolysis. The reaction conditions were as follows: Glycerol: 3 g (10 wt %); Catalyst: 0.25 g; Temp.: 200° C. (473 K); P$_{H2}$: 41 bar; Solvent: H$_2$O; Liq. Volume: 30 ml; and Time: 6 hours. FIG. 6 shows glycerol hydrogenolysis with Ru-PTA-Y, Ru-APTS-Y, and Ru/Al$_2$O$_3$. Ru-PTA-Y is shown to be the superior catalyst.

Figure 7:
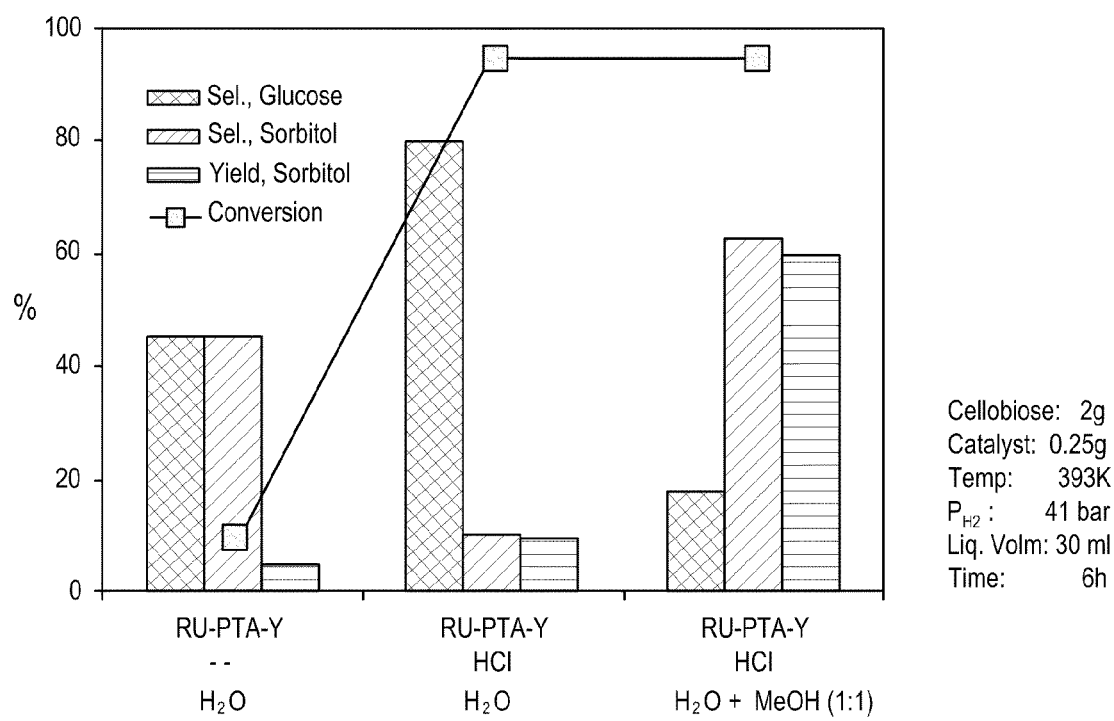
FIG. 7 is a graph that shows the conversion, yield, and selectivity for sorbitol from cellobiose hydrogenolysis with various liquid reaction mixtures.

The Ru-PTA-Y catalyst was also analyzed in an aqueous reaction medium with water and with or without HCl as well as with HCl and methanol as a co-solvent. Briefly, 2 g of cellobiose was combined with 0.25 g of catalyst in the reaction liquid (30 ml) and reaction carried out for 6 hours at 120° C. (393 K) at P$_{H2}$ at 41 bar. The results are shown in FIG. 7, which indicate that the use of HCl and methanol as a co-solvent improves selectivity and yield of sorbitol, as well as the selectivity for sorbitol.

Figure 8:
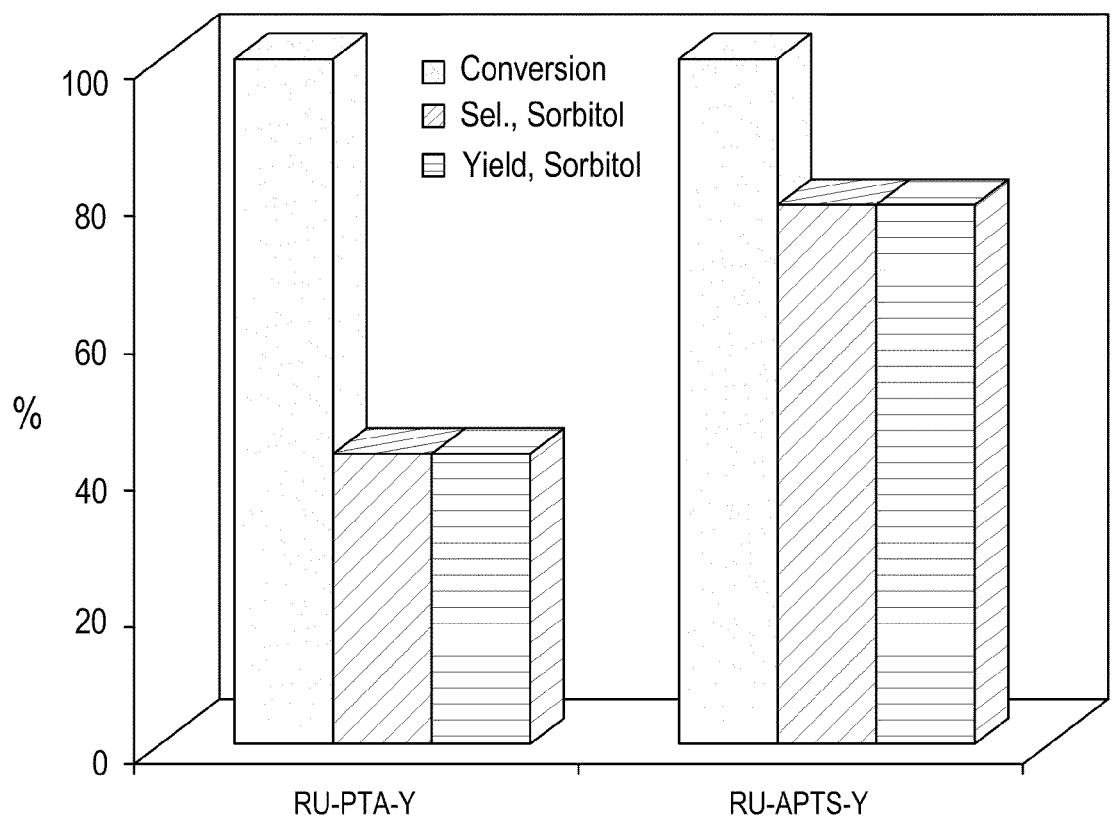
FIG. 8 is a graph that shows the differences in conversion, yield, and selectivity for sorbitol from cellobiose hydrogenolysis between Ru-PTA-Y and Ru-APTS-Y catalysts. The reaction conditions were as follows: Cellobiose: 2 g; catalyst: 0.25 g; HCl: 0.25 ml; temp: 120° C. (393 K), P$_{H2}$: 41 bar; solvent: H$^2$O+MeOH (1:1); liquid volume: 30 ml; time: 6 h.

The Ru-PTA-Y and Ru-APTS-Y catalysts were studied with regard to cellobiose hydrogenolysis. Briefly, the reaction was as follows: Cellobiose: 2 g; Catalyst: 0.25 g; HCl: 0.25 ml; Temp.: 120° C. (393 K); P$_{H2}$: 41 bar; Solvent: H$_2$O+ MeOH (1:1); Liquid Volume: 30 ml; and Time: 6 hours. With regard to hydrogenolysis of cellobiose, FIG. 8 shows that the Ru-APTS-Y catalyst appears to be superior.

In view of the foregoing, it was found that Ru-PTA-Y showed improved performance compared to Ru/Al$_2$O$_3$ for glycerol hydrogenolysis to 1,2-PDO. Also, immobilization with APTS showed higher sorbitol selectivity from cellobiose compared to PTA based catalyst.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A catalyst composition comprising:
   a. a support;
   b. a ruthenium catalyst (Ru) nanoparticle; and
   c. a linker linking the Ru nanoparticle to the support, wherein the linker is stable under hydrogenolysis conditions.

2. The catalyst composition of claim 1, wherein the linker includes 3-aminopropyl trimethoxysilane, and derivatives thereof with amine functionality.

3. The catalyst composition of claim 1, wherein the linker includes phosphotungstic acid or other solid acid agent.

4. The catalyst composition of claim 1, wherein the support is selected from alumina, carbon, silica, a zeolite, $TiO_2$, $ZrO_2$, or another suitable material.

5. The catalyst composition of claim 1, wherein the support includes NaY zeolite.

6. The catalyst composition of claim 1, wherein the nanoparticle has a size range from about 1 nm to about 25 nm.

7. The catalyst composition of claim 1, comprising a plurality of Ru catalysts linked to the support through a plurality of linkers.

8. The catalyst composition of claim 7, wherein the Ru catalysts are linked to the support in a distribution configured to inhibit agglomeration of the Ru catalysts.

9. The catalyst composition of claim 8, wherein the support is a macro support structure.

10. The catalyst composition of claim 9, wherein the macro support structure has a dimension from about 1 micron or greater.

11. The catalyst composition of claim 9, wherein the linker is stable at temperatures ranging from about 80° C. to about 400° C.

12. A hydrogenolysis reaction composition comprising:
    a. the catalyst composition of claim 1; and
    b. a cellulose, cellobiose, polyol, or dehydration product thereof.

13. The hydrogenolysis reaction composition of claim 12, further comprising water.

14. The hydrogenolysis reaction composition of claim 13, further comprising an alcohol.

15. The hydrogenolysis reaction composition of claim 14, wherein the alcohol is selected from C1-C3 alcohols, methanol, ethanol, isopropanol, and combinations thereof.

16. The catalyst composition of claim 14, further comprising an acid.

17. The catalyst composition of claim 16, wherein the acid is selected from hydrochloric acid, sulfuric acid, nitric acid, acetic acid, oxalic acid, p-toluene sulfonic acid, and combinations thereof.

18. A hydrogenolysis process comprising:
    a. providing the catalyst composition of claim 1;
    b. combining the catalyst with liquid phase reactants having one or more of water, an alcohol, or an acid and with a reactant selected from cellulose, cellobiose, polyol, dehydration product thereof, or combinations thereof;
    c. introducing hydrogen into the liquid phase; and
    d. reacting the reactants with the catalyst in the presence of hydrogen to form an alcohol, lower polyol, or higher polyol, wherein cellulose and cellobiose reactants form higher polyols, and polyol and polyol dehydration products form alcohols and lower polyols.

19. The process of claim 18, wherein the reactant in the liquid phase from about 1% to about 15% by weight or volume.

20. The process of claim 18, wherein the alcohol ranges from about 30% to about 50% by weight or volume of the reaction liquid.

21. The process of claim 18, wherein the acid ranges from about 1% to about 5% by weight or volume of the reaction liquid.

22. The process of claim 18, wherein the reaction is conducted at a temperature from about 80° C. to about 400° C.

23. The process of claim 18, wherein the reaction is conducted at a pressure of about 10 bar to about 300 bar.

24. The process of claim 18, wherein conversion of the limiting reactant is greater than 90 mole %.

25. The process of claim 18, wherein selectivity during the conversion of the cellulose or cellobiose to sorbitol ranges from 50 mole % to 75 mole %.

26. A method of synthesizing the catalyst composition of claim 1, the method comprising:
    a. providing the support;
    b. providing the Ru nanoparticle; and
    c. linking the linker to the Ru nanoparticle and to the support so as to link the Ru nanoparticle to the support, wherein the linker is stable under hydrogenolysis conditions.

27. The method of claim 26, further comprising preparing the Ru nanoparticle from a Ru salt.

28. The method of claim 27, wherein the preparation of the Ru nanoparticle is by reduction of the Ru salt.

29. A method of claim 26, wherein the linker includes 3-aminopropyl trimethoxysilane or derivative thereof with amine functionality, wherein the 3-aminopropyl trimethoxysilane linker is stable under hydrogenolysis conditions.

30. A method of claim 26, wherein the linker includes phosphotungstic acid or other solid acid agent, wherein the phosphotungstic acid linker is stable under hydrogenolysis conditions.

* * * * *